United States Patent
Meriläinen et al.

[19]

[11] Patent Number: 5,608,212

[45] Date of Patent: Mar. 4, 1997

[54] METHOD FOR CALIBRATING THE ZERO POINT IN A GAS ANALYZER

[75] Inventors: Timo Meriläinen; Börje Rantala, both of Helsinki; Kurt Weckström, Espoo; Kai Karlsson, Helsinki, all of Finland

[73] Assignee: Instrumentarium Corp., Finland

[21] Appl. No.: 360,258

[22] Filed: Dec. 20, 1994

[30] Foreign Application Priority Data

Dec. 22, 1993 [FI] Finland ................................. 935788

[51] Int. Cl.[6] ........................................... G01N 21/61
[52] U.S. Cl. ........................................ 250/252.1; 250/343
[58] Field of Search ........................... 250/252.1 A, 343

[56] References Cited

U.S. PATENT DOCUMENTS

| 4,153,837 | 5/1979 | Ross | 250/343 |
|---|---|---|---|
| 4,398,091 | 8/1983 | Passaro | 250/343 |
| 4,480,191 | 10/1984 | Karpowycz | 250/343 |
| 4,687,934 | 8/1987 | Passaro et al. | 250/252.1 A |
| 4,692,621 | 9/1987 | Passaro et al. | 250/343 |
| 4,918,311 | 4/1990 | Rogers | 250/343 |
| 5,231,591 | 7/1993 | Flewelling et al. | 128/719 |

*Primary Examiner*—Carolyn E. Fields
*Attorney, Agent, or Firm*—Andrus, Sceales, Starke & Sawall

[57] ABSTRACT

A method for calibrating a gas analyzer (1). A gas analyzer is calibrated by measuring the zero level of the analyzer (1). The level of the analyzer is measured, after a preceding reset, whenever a temperature variation ($\Delta T$) of an infrared sensor (14) included in the analyzer (1) or of a component thermally connected in a highly conductive manner thereto exceeds a predetermined threshold value (A), or the temperature variation rate (D) of the infrared sensor (14) of the analyzer (1) or of a component thermally connected in a highly conductive manner thereto exceeds a predetermined limit valve.

22 Claims, 3 Drawing Sheets

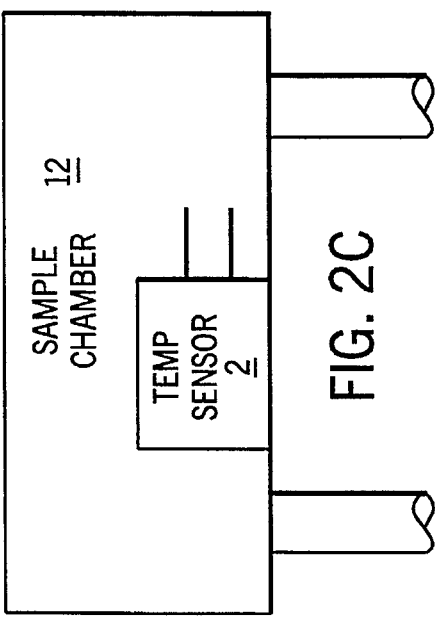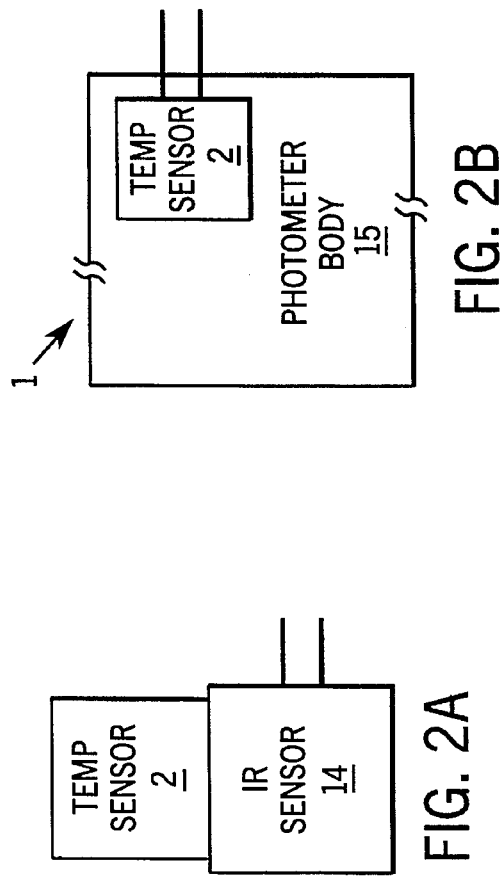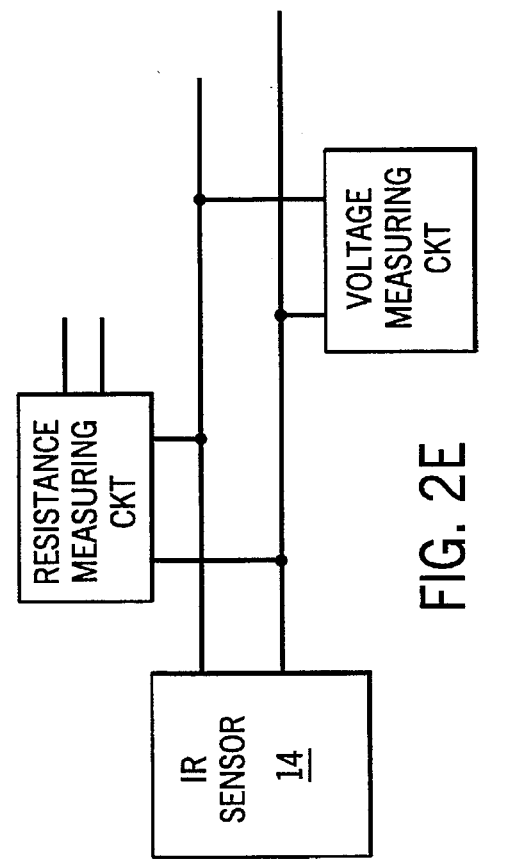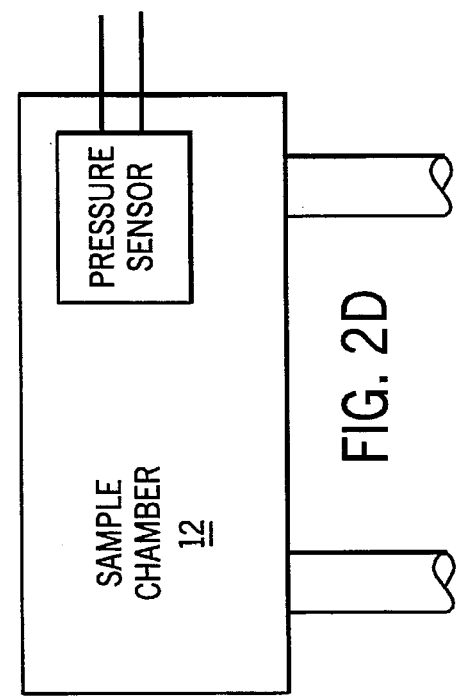

METHOD FOR CALIBRATING THE ZERO POINT IN A GAS ANALYZER

The present invention relates to a method for calibrating the zero point in a gas analyzer.

According to the prior art, the infrared sensor of a respiratory gas analyzer based on the infrared absorption of gases is accessible to radiation over the absorption band of a gas to be determined. In view of calculating the concentration of a gas to be determined, the permeability of a sample is measured:

$$T(c)=[V(c)-Vd]/[V(0)Vd],$$

wherein $T(c)$=permeability $V(c)$=the sensor output voltage when the concentration of a gas to be determined=c.

$Vd$=dark level=the sensor output voltage when no radiation is admitted through a sample to the infrared sensor $V(0)$=zero level=the sensor output voltage when the concentration of a gas to be determined=0.

Thus, the measurement of concentration requires that the zero level is known. However, the zero level will change along with a change in the temperature of an infrared source or sensor or as a result of the thermal expansion of mechanical components or the thermal drifts of measuring electronics. The zero level is also affected by changes in the characteristics of the mechanical dimensions and optical components of an analyzer.

Gas analyzers generally employ structural design for continuously measuring the approximative value of a zero level.

In double-beam measurement, the measuring beam is directed through both a sample chamber and a reference chamber not containing the gas to be determined onto a measuring sensor or a separate reference sensor. Guiding a reference beam and a measuring beam alternately to the same sensor requires movable mechanical components, which increase the bulk and price of the analyzer and impair its reliability. A drawback in the use of a reference sensor is the requirement of exactly matching the properties of a reference sensor and those of a measuring sensor.

It is also possible to use a reference beam directed through a sample chamber on a wavelength with no absorption for the gas to be determined. Since the sensor is alternately accessible to a measuring beam and to a reference beam, this requires movable mechanical components which lead to an increased price and bulk and an impaired reliability.

The above-described methods are capable of effecting a sufficiently accurate short-term correction of the zero level but incapable of eliminating the slow drift of the zero level, which can be caused by a variation in the optical stability between a measuring and a reference chamber or in the spectral distribution of the radiation output of a source and the sensitivity of a sensor or by a disparity in the characteristics of a measuring and a reference sensor.

Even if one of the above-described zero-level (approximate) monitoring systems were in operation, the confirmation of measuring accuracy thus requires resets to zero for measuring the real zero level of an analyzer. The measured zero level is then used as an approximative value for the zero level until the next reset. The reset is effected according to the prior art automatically at predetermined constant time intervals. The reset interval can be shorter after the apparatus is actuated, for example such that the resets are effected after 5, 10, 20 and 40 minutes of operation and in continuous action at time intervals of 30 minutes.

For the duration of a reset operation, the sample chamber is filled with a reset gas and, therefore, the monitoring of a patient's respiratory gases is interrupted for several seconds. This constitutes a safety hazard and at least a distraction to the monitor operator. Thus, unnecessary resets should be avoided but, on the other hand, resets must be effected with sufficient frequency for the confirmation of measuring accuracy.

The zero point error is primarily caused by variations in the temperature of a gas analyzer. Resetting at fixed intervals leads to unnecessary resets if the temperature of a gas analyzer does not change. On the other hand, a rapid temperature variation, e.g. when transferring an analyzer from one room to another, produces a zero point error which is not corrected until the next reset operation up to 30 minutes later.

U.S. Pat. No. 4,692,621 discloses a digital anaesthesia analyzer wherein the analyzer is reset to zero on the basis of a variation in ambient air temperature. Since a variation in ambient temperature is just one of the factors affecting the analyzer temperature and, in addition, the analyzer temperature may remain stable notwithstanding a variation in ambient temperature, the arrangement disclosed in the cited patent leads to a lot of error conditions and unnecessary resets.

An object of this invention is to eliminate the deficiencies of the above-described technology and to provide an entirely novel type of method for calibrating the zero point in a gas analyzer and particularly in a respiratory gas analyzer.

The invention is based on measuring the zero level of an analyzer at least at those moments when a change in the analyzer temperature after the preceding reset exceeds a predetermined threshold value (A) or when a threshold value (B) for the variation rate of the analyzer temperature exceeds a predetermined limit value. The threshold value A may preferably be 3°–5° C. and the threshold value B may preferably be 0.2°–0.4° C./min.

Thus, the gas analyzer will be reset to zero if its temperature after the preceding reset has changed more than a predetermined reset threshold or if the analyzer temperature changes rapidly. If the temperature of a gas analyzer remains constant, the measuring accuracy can be confirmed by a reset effected at fixed intervals.

The invention is capable of providing substantial benefits. A simple apparatus can be used for achieving a high patient safety. Unnecessary calibrations are not carried out, but resetting is only effected when error probability is at its highest.

The invention will now be described in more detail with reference to exemplary embodiments shown in the accompanying drawing.

In the drawing:

FIGS. 2A–2I show alternative ways of carrying out a measuring step of the present invention.

Figure 1:
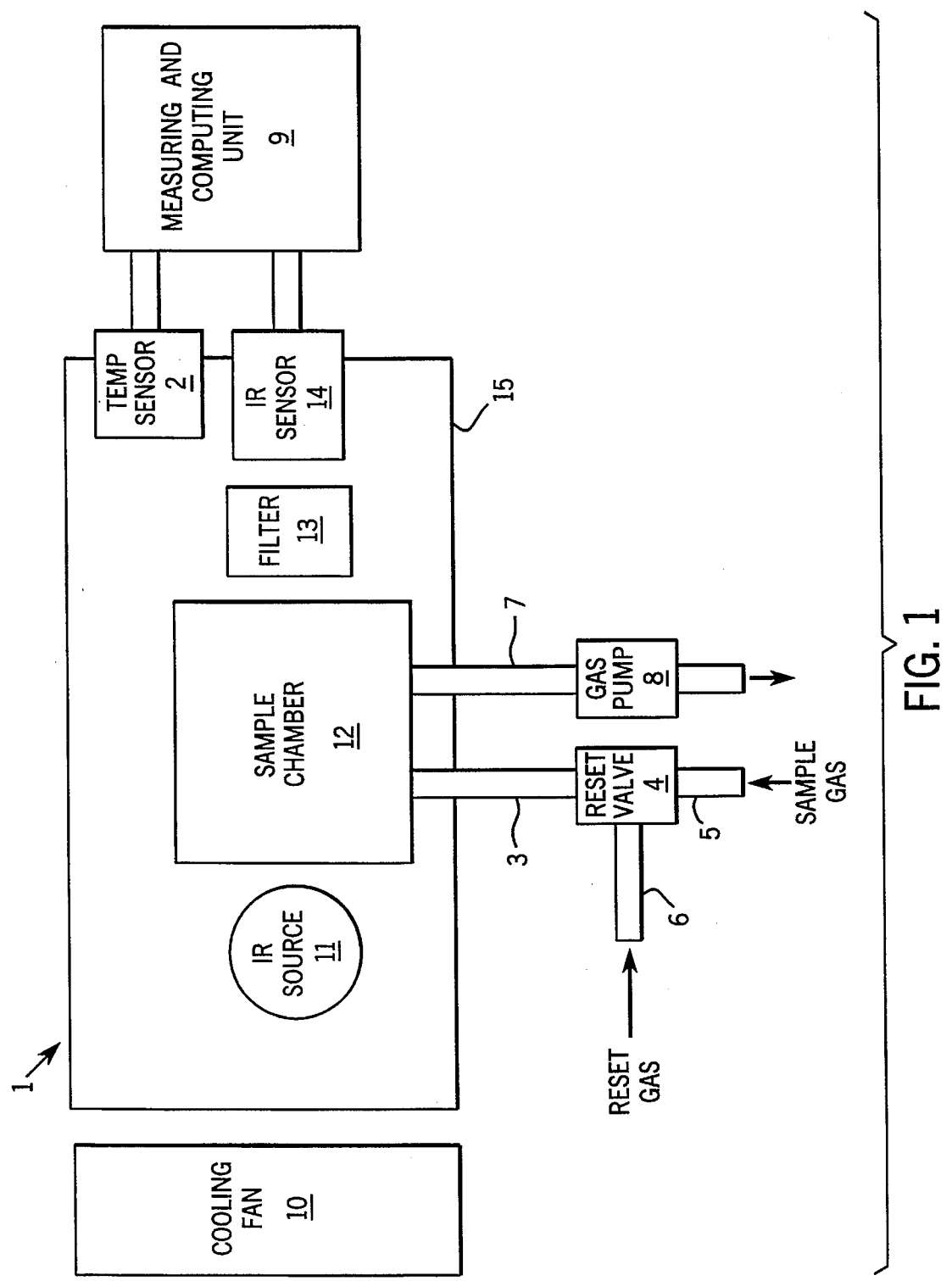
FIG. 1 shows a gas analyzer of the present invention.

As shown in the drawing, one embodiment for a gas analyzer of the invention comprises an infrared photometer 1, a measuring and computing element 9, a gas sample supply and discharge circuit as well as a cooling fan 10. The photometer 1 includes an infrared source 11, located at one end of a sample chamber 12. The other end of the sample chamber 12 is provided with an optical band-pass filter 13 and the traveling path of radiation from the infrared source 11 downstream of the band-pass filter 13 is provided with an infrared sensor 14. The infrared photometer 1 is fitted with a temperature sensor 2. The gas sample supply and discharge circuit comprises an inlet duct 3, connected to the sample chamber and provided with a reset valve 4. The reset valve 4 is further provided with a sample duct 5 and a reset gas duct 6. Preferably, the end of the sample chamber 12 facing towards the band-pass filter 13 is provided with an outlet duct 7, provided with a gas pump 8. The measuring and computing element 9 processes the signals from sensors 2 and 14 and the cooling fan 10 takes care of the cooling of photometer 1.

The gas pump 8 vacuums a gas sample to be analyzed into the sample chamber 12 of said photometer 1 through the sample duct 5, reset valve 4, inlet duct 3 and outlet duct 7. For the duration of resetting, the condition of the reset valve 4 is reversed in such a manner that, instead of the gas sample, the sample chamber 12 of the photometer 1 receives a resetting gas having an infrared absorption which is known on the measuring wavelength. The reset gas may preferably be indoor air.

The photometer has preferably such a mechanical configuration that the sample chamber 12, filter 13 and sensor 14 are as precisely as possible at the same temperature. This temperature is measured by means of the temperature sensor 2.

Voltage from the sensor 14 and a signal obtained from the temperature sensor 2 are delivered to the measuring and computing element 9, which measures the strength of these signals and uses the measuring data for calculating the concentration of the gas subjected to determination.

According to the invention, an analyzer is reset to zero, if:

$$\Delta T > \Delta T_{min} \text{ and } t_{min} < t < t_{max} \text{ or} \quad (1)$$

$$D > D_{min} \text{ and } t_{min} < t < t_{max} \text{ or} \quad (2)$$

$$t = t_{max} \quad (3)$$

wherein $\Delta T$=temperature change since preceding reset $\Delta T_{min}$=threshold value A D=temperature variation rate $D_{min}$=threshold value B t=time lapsed since resetting $t_{min}$=minimum value for reset interval $t_{max}$=maximum value for reset interval Thus, resetting is effected if the temperature change measured by the temperature sensor 2 after the preceding reset exceeds threshold value A or if the variation rate of temperature exceeds threshold value B or if the time lapse since the preceding reset equals $t_{max}$. The maximal reset interval may exceed the prior art reset interval. A maximal reset interval according to the invention suitable for respiratory gas analyzers can be 2–4 hours.

When applying the method of the invention, it is preferred that a gas analyzer be heated as rapidly as possible to its operating temperature. This can be accomplished, e.g., such that the infrared source 11 of the gas analyzer 1 is operated for the duration of a heating period at a higher-than-normal capacity and the analyzer cooling fan 10 is simultaneously maintained out of action.

A method of the invention is applicable in gas analyzers in which the zero point error is primarily caused by temperature fluctuations and in which the temperatures of heat sensitive components preferably vary the same way.

The operating principle and configuration of an analyzer do not affect the applicability of the method.

Figure 2H:
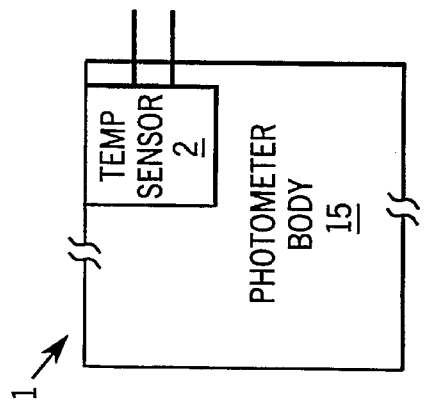

The primary variable upon which a resetting decision is based, is the internal temperature of an analyzer and especially the temperature of an infrared sensor (see FIG. 2A) or an element thermally connected in a highly conductive manner thereto. According to the invention, a preferred measuring target is the body or frame of an analyzer (see FIG. 1). Naturally, instead of this, it is possible to measure for example the internal temperature of a monitor (see FIG. 2B) or even the temperature of a gas sample arriving in an analyzer (see FIG. 2C), all of these having an effect on the temperature of an analyzer or reflecting it indirectly.

The reset timing method of the invention can be carried out without a temperature sensor by measuring a quantity other than temperature, that quantity changing along with temperature. These may include for example the pressure prevailing in the reference chamber of an analyzer (see FIG. 2D), the dark resistance of an infrared sensor or a supplementary component induced in the output voltage of a sensor by a temperature variation (see FIG. 2E).

Figure 2G:
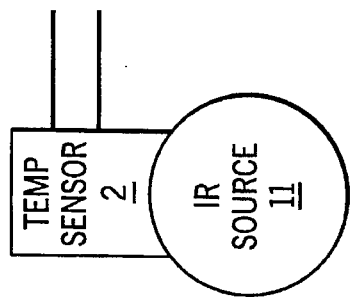

In analyzers with the temperatures of components responsible for zero point error not changing the same way it is possible to measure separately the temperature of each component (see FIG. 2F) and to effect a reset if the componentwise predetermined threshold values A or B are exceeded in one component.

Figure 2I:
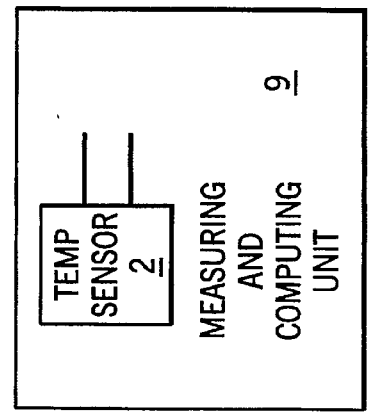
Figure 2F:
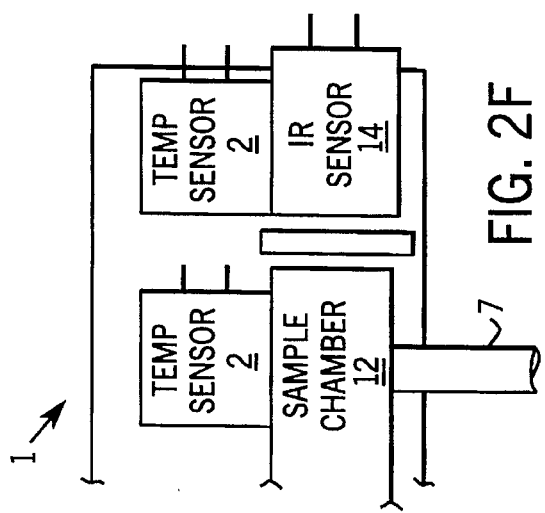

Suitable temperature measuring targets include for example the infrared source 11 (see FIG. 2G), infrared sensor 14, photometer body 15 (see FIG. 2H) as well as the heat sensitive components included in the measuring and computing element 9 (see FIG. 2I).

We claim:

1. A method for calibrating the zero point of a gas analyzer having an infrared sensor, said method comprising the steps of:

sequentially measuring a phenomenon indicative of temperature conditions in the gas analyzer capable of causing alteration of the zero point;

determining whether or not the amount of change of the measured phenomenon exceeds a threshold amount of change value and whether or not the rate of change of the measured phenomenon exceeds a threshold rate of change value; and carrying out a calibration of the zero point of the gas analyzer when one of the threshold values is exceeded, the time at which the calibration of the zero point is carried out being as follows: at the end of a minimum time period from a predetermined timing point if the threshold value is exceeded in the minimum time period; at the time when the threshold value is exceeded when same occurs after the end of the minimum time period and before a preselected maximum time from a predetermined starting point; or at the preselected maximum time from the predetermined starting point in the event the threshold value has not been exceeded before the maximum time.

2. The method as set forth in claim 1 wherein the predetermined timing point for determining when the calibration is carried out is a previous calibration of the zero point of the gas analyzer.

3. The method as set forth in claim 1 further defined as measuring temperatures indicative of the temperature conditions in the gas analyzer and wherein the determining step is further defined as determining whether or not the amount of change of the measured temperatures exceeds a temperature amount of change threshold value and whether or not the rate of change of the measured temperatures exceeds a temperature rate of change threshold value.

4. The method as set forth in claim 3 wherein the temperature amount of change threshold value comprises a temperature change of between 3°–5° C.

5. The method as set forth in claim 4 wherein the temperature rate of change threshold value is approximately 0.2°–0.4° C. per minute.

6. The method as set forth in claim 3 wherein the temperature rate of change threshold value is approximately 0.2°–0.4° C. per minute.

7. A method as set forth in claim 3 wherein the measuring step is further defined as measuring the temperature of the infrared sensor.

8. The method as set forth in claim 3 wherein the measuring step is further defined as measuring the temperature of an infrared source of the gas analyzer.

9. A method as set forth in claim 3 wherein the measuring step is further defined as measuring the temperature of an element of the gas analyzer connected to the infrared sensor in a thermally conductive manner.

10. The method according to claim 3 wherein the measuring step is further defined as measuring the temperature of a frame of the gas analyzer.

11. The method as set forth in claim 3 wherein the measuring step is further defined as measuring the temperature of a photometer body of the gas analyzer.

12. A method as set forth in claim 3 wherein the measuring step is further defined as measuring the temperature of components included in a measuring and computing element of the gas analyzer.

13. The method according to claim 3 wherein the measuring step is further defined as measuring the internal temperature of the gas analyzer.

14. A method as set forth in claim 3 wherein the measuring step is further defined as measuring the temperature of a gas sample supplied to the gas analyzer.

15. A method as set forth in claim 3 wherein the measuring step is further defined as measuring the temperature of a plurality of elements of the gas analyzer, wherein the determining step is carried out with respect to the measurements obtained from each of the elements, and wherein a calibration step is carried out when the temperatures of any one of the elements exceeds a threshold value.

16. The method as set forth in claim 1 wherein the measuring step is further defined as measuring a pressure prevailing in a reference chamber of the gas analyzer.

17. The method as set forth in claim 1 wherein the measuring step is further defined as measuring the electrical properties of the infrared sensor when no radiation is admitted through a gas sample to the infrared sensor.

18. The method according to claim 1 wherein the measuring step is further defined as measuring a component of the output voltage of the infrared sensor induced by the temperature conditions to which the infrared sensor is subjected.

19. A method as set forth in claim 1 wherein the gas analyzer is further defined as a respiratory gas analyzer.

20. A method as set forth in claim 1 further defined as including the steps of initially operating the infrared source at a higher-than-normal capacity and preventing operation of a cooling fan included in the analyzer, thereby to heat the analyzer to its operating temperature as rapidly as possible.

21. A method for calibrating the zero point of a respiratory gas analyzer having an infrared sensor, said method comprising the steps of:

sequentially measuring the temperature of the infrared sensor;

determining whether or not the amount of change of the temperature exceeds a temperature amount of change threshold value and whether or not the rate of change of the temperature exceeds a temperature rate of change threshold value; and carrying out a calibration of the zero point of gas analyzer when one of the threshold values is exceeded, the time at which the calibration of the zero point is carried out being as follows: at the end of a minimum time period from a predetermined timing point if the threshold value is exceeded in the minimum time period; at the time when the threshold value is exceeded when same occurs after the end of the minimum time period and before a preselected maximum time from a predetermined starting point; or at the preselected maximum time from the predetermined starting point in the event the threshold value has not been exceeded before the maximum time.

22. The method as set forth in claim 21 wherein the determining step is further defined as establishing a temperature change threshold value of approximately 3°–50° C. and as establishing a temperature rate of change threshold value of approximately 0.2°–0.4° C. per minute.

* * * * *